United States Patent
Saleh et al.

(10) Patent No.: US 10,456,391 B2
(45) Date of Patent: Oct. 29, 2019

(54) COMPOSITIONS AND METHODS FOR TREATING CARDIOMETABOLIC DISEASES AND DISORDERS

(71) Applicant: University of Prince Edward Island, Charlottetown (CA)

(72) Inventors: Tarek Saleh, Stratford (CA); Bobby Khan, Alpharetta, GA (US); Nadya Merchant, Atlanta, GA (US)

(73) Assignee: University of Prince Edward Island, Charlottetown, Prince Edward Island (CA)

( * ) Notice: Subject to any disclaimer, the term of this patent is extended or adjusted under 35 U.S.C. 154(b) by 0 days.

(21) Appl. No.: 14/890,708

(22) PCT Filed: May 14, 2013

(86) PCT No.: PCT/CA2013/000472
§ 371 (c)(1),
(2) Date: Nov. 12, 2015

(87) PCT Pub. No.: WO2014/183184
PCT Pub. Date: Nov. 20, 2014

(65) Prior Publication Data
US 2016/0082000 A1    Mar. 24, 2016

(51) Int. Cl.
*A61K 36/68* (2006.01)
*A61K 31/473* (2006.01)
*A61K 31/385* (2006.01)
*A61K 31/12* (2006.01)
*A61K 31/4375* (2006.01)
(Continued)

(52) U.S. Cl.
CPC ............ *A61K 31/473* (2013.01); *A23L 33/10* (2016.08); *A23L 33/16* (2016.08); *A61K 31/12* (2013.01); *A61K 31/385* (2013.01); *A61K 31/4375* (2013.01); *A61K 36/68* (2013.01); *A23V 2002/00* (2013.01)

(58) Field of Classification Search
CPC ... A61K 31/473; A61K 31/4375; A23L 33/10; A23L 33/16
See application file for complete search history.

(56) References Cited

FOREIGN PATENT DOCUMENTS

| EP | 935962 | 2/1999 |
|---|---|---|
| WO | WO-1997/019679 | 6/1997 |

(Continued)

OTHER PUBLICATIONS

Clinical Trials (https://clinicaltrials.gov/archive/NCT01696448/2012_09_28, accessed Apr. 17, 2017, published Sep. 28, 2012).*

(Continued)

*Primary Examiner* — Angela C Brown-Pettigrew
(74) *Attorney, Agent, or Firm* — Howson & Howson LLP (57) ABSTRACT

Described herein are combinations useful for treating or preventing a cardiometabolic disease or disorder, or which can be used for appetite suppression, for improvement of endothelial function, for controlling weight, or a combination of one or more thereof. The combinations comprise Berberine, alpha lipoic acid (LA), and apocynin, or an isomer, derivative, pharmaceutically acceptable salt or ester of one or more thereof. Methods of treatment using the combinations, as well as compositions and related medical uses are also described.

7 Claims, 3 Drawing Sheets

(51) Int. Cl.
*A23L 33/10* (2016.01)
*A23L 33/16* (2016.01)

(56) References Cited

FOREIGN PATENT DOCUMENTS

WO  WO-1999/055331  11/1999
WO  WO-2011/119649  9/2011

OTHER PUBLICATIONS

Thirunavukkarasu et al (Experimental Diab. Res., 5:195-200, 2004).*
Lee et al (Fitoterapia 77 (2006) 579-584).*
Lee et al (Diabetes, vol. 55, Aug. 2006).*
Zhang et al (J Clin Endocrinol Metab, Jul. 2008, 93(7):2559-2565).*
Sheila a Doggrell (2005) Berberine—a novel approach to cholesterol lowering, Expert Opinion on Investigational Drugs, 14:5, 683-685.*
Kathiresan et al, Cell. Mar. 16, 2012; 148(6): 1242-1257 (Year: 2012).*
International Search Report, dated Jan. 6, 2014, issued on corresponding International Patent Application No. PCT/CA2013/000472.
Ziegler et al., "Treatment of symptomatic diabetic peripheral neuropathy with the anti-oxidant α-lipoic acid", Diabetologia, vol. 38:1425-1433, Mar. 1995.
Koh et al., "Effects of alpha-lipoic Acid on body weight in obese subjects", Am. J. Med, vol. 124(1):85.e1-e8, Jan. 2011.

* cited by examiner

COMPOSITIONS AND METHODS FOR TREATING CARDIOMETABOLIC DISEASES AND DISORDERS

CROSS-REFERENCE TO RELATED APPLICATIONS

This application is a US national phase of International Patent Application No. PCT/CA2013/000472, filed May 14, 2013, which is incorporated herein by reference in its entirety.

FIELD OF INVENTION

The present invention relates to combinations of apocynin, lipoic acid and berberine, as well as the use of such combinations for treating or preventing cardiometabolic diseases, disorders or associated conditions.

BACKGROUND OF THE INVENTION

Chronic cardiometabolic disease has become a prominent public health concern. While medical treatment has been effective in the treatment of certain cardiometabolic diseases (including coronary atherosclerosis and diabetes mellitus), the incidence of these disorders continues to be high. Many reasons are responsible, but lifestyle changes, including an increased prevalence of obesity and the metabolic syndrome, are significant for this cause. Recent reported guidelines by the JNC-VII and National Cholesterol Education Panel/ATP-III suggest that blood pressure reduction is effective in improving the overall quality of life and may be helpful in the prevention of cardiovascular disease.

Diagnosis and treatment of obese patients with hypertension requires that health care providers address the issues of hypertension, glucose intolerance, body weight and dyslipidemia. Strategies to promote therapeutic lifestyle change (TLC), specifically increased physical activity and reduced dietary intake resulting in weight loss, are not as well defined. A sedentary lifestyle and poor cardiorespiratory fitness are not only associated with the (cardio) metabolic syndrome but could actually be considered features of the metabolic syndrome. These issues are significant in the health of certain individuals, who experience greater difficulty in treated BP control, experience increased hypertensive and diabetic complications, and have higher levels of obesity.

SUMMARY OF THE INVENTION

It is therefore an object of the invention to provide compositions and/or combinations of drugs that can be used to treat or prevent cardiometabolic diseases, disorders or other associated conditions.

Accordingly, the invention relates to a combination for treating or preventing a cardiometabolic disease or disorder, or which can be used for appetite suppression, for improvement of endothelial function, for controlling weight, or a combination of one or more thereof. The combination comprises Berberine, alpha lipoic acid (LA), and apocynin, or an isomer, derivative, pharmaceutically acceptable salt or ester of one or more thereof. The Berberine, LA and apocynin may be provided in purified form or as a component of a source material, and thus may be either synthetic or naturally derived.

The invention also relates to a commercial package comprising a combination of Berberine, LA, and apocynin, or an isomer, derivative, pharmaceutically acceptable salt or ester of one or more thereof, in effective amounts to treat or prevent a cardiometabolic disease or disorder, or which can be used for appetite suppression, for improvement of endothelial function, for controlling weight, or for a combination of one or more of these in a subject. Similar to the above combination, the Berberine, LA and apocynin may be synthetic or naturally derived, and provided in purified form or as a component of a source material.

There is also provided a method of treating or preventing a cardiometabolic disease or disorder, and/or for appetite suppression, improvement of endothelial function, controlling weight, or a combination thereof, the method comprising administering Berberine, LA, and apocynin, or an isomer, derivative, pharmaceutically acceptable salt or ester of one or more thereof, to a subject in need thereof in an amount sufficient to ameliorate or prevent said cardiometabolic disease or disorder, and/or to suppress appetite, improve endothelial function, control weight, or a combination thereof. Again, the Berberine, LA and apocynin may be synthetic or naturally derived, and provided in purified form or as a component of a source material.

Therapeutic uses of the above combination and commercial package are also provided, whereby the Berberine, LA, and apocynin, or an isomer, derivative, pharmaceutically acceptable salt or ester of one or more thereof, are used for treating or preventing a cardiometabolic disease or disorder, and/or for appetite suppression, improvement of endothelial function, controlling weight, or a combination thereof.

Other features and advantages of the present application will become apparent from the following detailed description. It should be understood, however, that the detailed description and the specific examples while indicating embodiments of the application are given by way of illustration only, since various changes and modifications within the spirit and scope of the application will become apparent to those skilled in the art.

BRIEF DESCRIPTION OF THE DRAWINGS

These and other features of the invention will become more apparent from the following description in which reference is made to the following drawings.

DETAILED DESCRIPTION

Described herein is a combination useful for treating or preventing a cardiometabolic disease or disorder, or which can be used for appetite suppression, for improvement of endothelial function, for controlling weight, or a combination of one or more thereof. The combination comprises Berberine, alpha lipoic acid (LA), and apocynin, or an isomer, derivative, pharmaceutically acceptable salt or ester of one or more thereof.

The Berberine, LA and apocynin may be provided in purified form or as a component of a source material, and thus may be either synthetic or naturally derived. In certain non-limiting embodiments, the source of apocynin may be *Picrorhiza* sp, or the root of the Canadian hemp plant (*Apocynum cannibum*).

If the apocynin source is a natural source such as *Picrorhiza*, those of skill in the art will appreciate that other components of the organism may also be present in addition to the apocynin compound itself, such as, in the case of *Picrorhiza*, Picroside I, II and kutkoside.

In particular examples of the above-described combination, which are not intended to be limiting, the combination may be formulated in one or more dosage form effective for administering from 100 mg to 400 mg Berberine, from 75 mg to 300 mg LA and from 50 mg to 200 mg *Picrorhiza* per dose. The combination may be prepared for administration up to 5 times daily, or potentially more frequently, although it is generally preferred (e.g. for patient compliance reasons) to administer less frequently, such as 1, 2 or 3 times daily. In certain embodiments, it may be preferred to formulate the dosages such that three daily doses can be taken, e.g. before breakfast, lunch and dinner.

In a particular example of the above combination, which is non-limiting, the dosages may be about 200 mg Berberine, about 150 mg LA, and about 100 mg *Picrorhiza*. In this example, the combination is particularly useful for administering 3 times a day, e.g. before breakfast, lunch and dinner. If taking before meals, the dosages will typically be taken anywhere within about an hour before, more particularly about 30 minutes before eating.

It is envisioned that the combination may be formulated in a number of ways. For example, without wishing to be limiting, the combination may be formulated as an oral supplement, as a food/feed additive, or as a pharmaceutical or nutraceutical composition. The combination may therefore further comprise one or more acceptable additives, carriers or excipients suitable for preparation of the desired dosage form(s).

The Berberine, LA and apocynin components of the combination may be administered together, or separately to obtain similar health benefits. Thus, there is also provided a commercial package comprising a combination of Berberine, LA, and apocynin, or an isomer, derivative, pharmaceutically acceptable salt or ester of one or more thereof, in effective amounts to treat or prevent a cardiometabolic disease or disorder, or for appetite suppression, for improvement of endothelial function, for controlling weight, or a combination thereof. The sources and quantities of the Berberine, LA and apocynin are similar to those described above in connection with the described combination.

In embodiments of the commercial package, it is feasible that each of the Berberine, LA, and apocynin components may be formulated separately, and provided as individual dosages. On the other hand, two, or even all three of these components may be combined or otherwise formulated together. Thus, a dosage may include one, two, or three tablets, capsules, or other dosage form, each formulated and packaged to allow the user to take the appropriate amounts of each component of the drug combination.

Thus, in a similar manner to that described above with reference to the combination, the commercial package may in certain non-limiting embodiments comprise at least one dosage comprising from 100 mg to 400 mg Berberine, from 75 mg to 300 mg LA and from 50 mg to 200 mg *Picrorhiza*, in combined or separate dosages that can be administered, e.g. up to 5, more preferably up to 3 times daily.

In an example of one non-limiting embodiment, the commercial package may contain at least one dosage comprising 200 mg Berberine, 150 mg LA, and 100 mg *Picrorhiza.*, such dosage(s) being particularly useful to administer up to 3 times daily, e.g. about an hour, more particularly about 30 minutes before breakfast, lunch and dinner.

As with the above-described combination, the dosages in the commercial package may be formulated in a number of ways. For example, without wishing to be limiting, they may be formulated as an oral supplement, as a food/feed additive, or as pharmaceutical or nutraceutical compositions. As indicated above, the Berberine, LA, and apocynin contained in the commercial package may be individually or separately formulated, and thus may be formulated or combined with one or more acceptable additives, carriers or excipients suitable for preparation of the desired dosage form(s).

The combination, compositions and commercial package containing Berberine, LA, and apocynin can be employed in methods of treating or preventing a cardiometabolic disease or disorder, for appetite suppression, improvement of endothelial function, controlling weight, or a combination thereof. Such methods comprise administering the Berberine, LA, and apocynin, or an isomer, derivative, pharmaceutically acceptable salt or ester of one or more thereof, to a subject in need thereof in an amount sufficient to ameliorate or prevent the cardiometabolic disease or disorder, and/or to suppress appetite, improve endothelial function, control weight, or a combination thereof.

Therapeutic uses of the combination, compositions and commercial package containing Berberine, LA, and apocynin are also provided, whereby the Berberine, LA, and apocynin, or isomer, derivative, pharmaceutically acceptable salt or ester thereof, are used for treating or preventing a cardiometabolic disease or disorder, and/or for appetite suppression, improvement of endothelial function, controlling weight, or a combination thereof.

In embodiments of the above methods and therapeutic uses, the Berberine, LA, and apocynin and dosages thereof are as described above.

Specific examples of the cardiometabolic disease or disorder include, but are not limited to hypercholesterolemia, dyslipidemia, obesity, insulin resistance, and hypertension.

The combination of compounds described herein is suitably formulated into one or more than one separate pharmaceutical compositions for administration to subjects in a biologically compatible form suitable for administration in vivo. Accordingly, the present application also includes a pharmaceutical composition comprising one or more compounds of the combination and a pharmaceutically acceptable carrier.

The compounds of the combination may be administered to a subject in a variety of forms depending on the selected route of administration, as will be understood by those skilled in the art. A compound may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time. Conventional procedures and ingredients for the selection and preparation of suitable compositions are described, for example, in Remington's Pharmaceutical Sciences (2000-20th edition) and in The United States Pharmacopeia: The National Formulary (USP 24 NF19) published in 1999.

The combination may be orally administered, for example, with an inert diluent or with an assimilable edible carrier, or the compounds may be enclosed in hard or soft shell gelatin capsules, compressed into tablets, or incorporated directly with the food of the diet. For oral therapeutic administration, the compound may be incorporated with excipient and used in the form of ingestible tablets, buccal tablets, troches, capsules, elixirs, suspensions, syrups, wafers, and the like. Oral dosage forms also include modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., as of molecular sieving type particles, or, a fine hollow permeable fiber bundle, or chopped hollow permeable fibers, agglomerated or held in a fibrous packet. In an embodiment, coatings that inhibit degradation of the compounds of the application by esterases, for example plasma esterases, are used in the oral administration forms. Timed-release compositions can be formulated, e.g. liposomes or those wherein the active compound is protected with differentially degradable coatings, such as by microencapsulation, multiple coatings, etc. Liposome delivery systems include, for example, small unilamellar vesicles, large unilamellar vesicles and multilamellar vesicles. Liposomes can be formed from a variety of phospholipids, such as cholesterol, stearylamine or phosphatidylcholines.

It is also possible to freeze-dry the compounds of the combination and use the lyophilizates obtained, for example, for the preparation of products for injection.

Compounds of the combination may also be administered parenterally. Solutions of one or more compounds can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as a fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

Compounds of the combination may also be delivered by the use of monoclonal antibodies as individual carriers to which the compound molecules are coupled. Compounds of the combination may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, compounds of the combination may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

Compounds of the combination may be used alone or in combination with other known agents useful for treating cardiometabolic diseases, disorders or associated conditions. Compounds of the combination may also be used in combination with agents that inhibit esterases, such as plasma esterases. When used in combination with other agents useful in treating cardiometabolic diseases, disorders or associated conditions, it is an embodiment that the compounds of the combination are administered contemporaneously with those agents. As used herein, "contemporaneous administration" of two substances to a subject means providing each of the two substances so that they are both biologically active in the individual at the same time. The exact details of the administration will depend on the pharmacokinetics of the two substances in the presence of each other, and can include administering the two substances within a few hours of each other, or even administering one substance within 24 hours of administration of the other, if the pharmacokinetics are suitable. Design of suitable dosing regimens is routine for one skilled in the art. In particular embodiments, two substances will be administered substantially simultaneously, i.e., within minutes of each other, or in a single composition that contains both substances. In a further embodiment, a combination of agents may be administered to a subject in a non-contemporaneous fashion.

The dosage of compounds can vary depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the subject to be treated. One of skill in the art can determine the appropriate dosage based on the above factors. Compounds of the application may be administered initially in a suitable dosage that may be adjusted as required, depending on the clinical response. As a representative example, oral dosages of one or more compounds of the application will range between about 1 mg per day to about 1000 mg per day for an adult, suitably about 1 mg per day to about 500 mg per day, more suitably about 1 mg per day to about 200 mg per day. In an embodiment of the application, compositions are formulated for oral administration and the compounds are suitably in the form of tablets containing 0.25, 0.5, 0.75, 1.0, 5.0, 10.0, 20.0, 25.0, 30.0, 40.0, 50.0, 60.0, 70.0, 75.0, 80.0, 90.0, 100.0, 150, 200, 250, 300, 350, 400, 450, 500, 550, 600, 650, 700, 750, 800, 850, 900, 950 or 1000 mg of active ingredient per tablet. Compounds of the application may be administered in a single daily dose or the total daily dose may be divided into two, three or four daily doses.

Treatment or prevention methods comprise administering to a subject or a cell, a therapeutically effective amount of the compounds of the combination, and optionally consists of a single administration, or alternatively comprises a series of administrations.

In an embodiment, the compounds may be administered to the subject in a series of administrations, for example about 1, 2, 3, 4, 5 or 6 times daily for 1 or more days either before or after the onset of the disease, disorder or condition. The length of the treatment period depends on a variety of factors, such as the cause of the disease, disorder or condition, severity of the disease, disorder or condition, the age of the subject, the concentration of the compounds, the activity of the compounds, and/or a combination thereof. It will also be appreciated that the effective dosage of the compound used for the treatment or prevention may increase or decrease over the course of a particular treatment or prevention regime. Changes in dosage may result and become apparent by standard diagnostic assays known in the art. In some instances, chronic administration may be required. For example, the compounds are administered to the subject in an amount and for a duration sufficient to treat the subject.

Definitions

Unless otherwise indicated, the definitions and embodiments described in this and other sections are intended to be applicable to all embodiments and aspects of the application herein described for which they are suitable as would be understood by a person skilled in the art.

Terms of degree such as "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The term "derivative" as used herein refers to a compound that is derived from a parent compound by modification of one or more of the functional groups in the parent molecule. For example, a derivative of LA may be a reduced form (dithiol) of LA, or a reduced form in which the thiol groups are substituted with, for example, a $C_{1-6}$ alkyl group or a $C_{1-6}$ acyl group. Further, a derivative of apocynin may be a compound wherein the keto group is oxidized (for example to the α-ketoacid) or reduced (to the corresponding alcohol). The term "subject" as used herein includes all members of the animal kingdom including mammals, and suitably refers to humans.

The term "pharmaceutically acceptable" means compatible with the treatment of subjects, in particular humans.

The term "pharmaceutically acceptable salt" means an acid addition salt which is suitable for, or compatible with, the treatment of patients.

The term "acid addition salt which is suitable for, or compatible with, the treatment of patients" as used herein means any non-toxic organic or inorganic salt of any basic compound. Basic compounds that form an acid addition salt include, for example, compounds comprising a thiol group. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, acid addition salts are more soluble in water and various hydrophilic organic solvents, and generally demonstrate higher melting points in comparison to their free base forms. The selection of the appropriate salt will be known to one skilled in the art.

The formation of a desired compound salt is achieved using standard techniques. For example, the basic compound is treated with an acid in a suitable solvent and the formed salt is isolated by filtration, extraction or any other suitable method.

The term "solvate" as used herein means a compound or its pharmaceutically acceptable salt, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate". The formation of solvates will vary depending on the compound and the solvate. In general, solvates are formed by dissolving the compound in the appropriate solvent and isolating the solvate by cooling or using an antisolvent. The solvate is typically dried or azeotroped under ambient conditions.

In embodiments of the described invention, compounds of the combination described herein have at least one asymmetric center. These compounds exist as enantiomers. Where compounds possess more than one asymmetric center, they may exist as diastereomers. It is to be understood that all such isomers and mixtures thereof in any proportion are encompassed within the scope of the present application. It is to be further understood that while the stereochemistry of the compounds may be as shown in any given compound listed herein, such compounds may also contain certain amounts (e.g. less than 20%, suitably less than 10%, more suitably less than 5%) of compounds of the application having alternate stereochemistry. For example, compounds that are described or shown without any stereochemical designations are understood to be racemic mixtures. However, it is to be understood that all enantiomers and diastereomers are included within the scope of the present application, including mixtures thereof in any proportion.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "treatment" as used herein also include prophylactic treatment. For example, a subject with early cardiometabolic disease can be treated to prevent progression, or alternatively a subject in remission can be treated with a combination or composition as described herein to prevent recurrence. Treatment methods comprise administering to a subject a therapeutically effective amount of the combination of compounds described. As used herein, the term "effective amount" or "therapeutically effective amount" means an amount effective, at dosages and for periods of time necessary to achieve the desired result. Effective amounts may vary according to factors such as the disease state, age, sex and/or weight of the subject. The amount of a given compound that will correspond to such an amount will vary depending upon various factors, such as the given drug or compound, the pharmaceutical formulation, the route of administration, the type of condition, disease or disorder, the identity of the subject being treated, and the like, but can nevertheless be routinely determined by one skilled in the art.

EXAMPLES

Example 1: The BANGALORE Study

In this study, the investigators evaluated the efficacy of the nutritional supplements berberine, alpha-lipoic acid, and *Picrorhiza* (CAR-191) when consumed 30 minutes before meals, on appetite suppression, body composition and weight control. Additionally, the investigators evaluated the effects of this combination of nutraceuticals on the mechanistic effects of oxidation, inflammation, and vascular function in a high-risk population with the metabolic syndrome.

The investigators evaluated the initiation of CAR-191 in patients which met at least 3 of the 5 criteria (ATP-III guidelines) for the cardiometabolic syndrome, and whether the CAR-191 combination as compared to placebo provides benefit in appetite suppression, body composition and certain clinical endpoints, including effects on endothelial function, lipid levels, and glucose control.

This study analyzed the effects of 12 week administration of CAR-191 versus placebo on these parameters in a population of patients (n=40) with the cardiometabolic syndrome. The study included a parallel design consisting of 2 weeks of washout and then 12 weeks of treatment to either CAR-191 or placebo. The total study period was 14 weeks. Patients were assigned to the CAR-191 or placebo group in a 3:1 ratio.

Primary Objective:
  To assess the comparative effect of a combination (known as CAR-191) of berberine (200 mg), alpha-lipoic acid (150 mg), and *Picrorhiza* (100 mg) three times a day, compared to placebo three times a day, on parameters relate to appetite suppression, weight control and body composition in a high risk population with the metabolic syndrome.

Secondary Co-Objectives:
  To evaluate the effects of CAR-191 versus placebo on changes in:
    Endothelial function using noninvasive brachial artery reactivity (BAR) ultrasound
    Biomarkers including IL-6, HOMA-IR, HbAlC, hsCRP, adiponectin, plasma/urine isoprostanes, PAI-1, TNFα-II, aldosterone, and glutathione redox ratio
    Urinary protein excretion
    Clinical chemistry including plasma glucose, blood urea nitrogen, creatinine, total bilirubin, uric acid, transaminases (SGOT/AST, SGPT/ALT), alkaline phosphatase, C-reactive protein, and lipoproteins Eligibility:
  Ages Eligible for Study: 18 Years to 80 Years
  Genders Eligible for Study: Both
  Accepts Healthy Volunteers: No Criteria:
Inclusion Criteria:
  Male and female subjects ≥18 years and ≤80 years with (cardio)metabolic syndrome as identified by investigators, OR
  Male and female subjects ≥18 years and ≤80 years with (cardio)metabolic syndrome defined by ATP-III criteria:
    Insulin resistance, identified by 1 of the following
    Type 2 diabetes with HgA1C<8.0% or on medical therapy
    Impaired fasting glucose
    Impaired glucose tolerance
    Or for those with normal fasting glucose levels (<100 mg/dl), glucose uptake below the lowest quartile for background population under investigation under hyperinsulinemic, euglycemic conditions
  Plus any 2 of the following:
    Plasma triglycerides≤150 mg/dl (≤1.7 mmol/L)
    HDL cholesterol <35 mg/dl (<0.9 mmol/L) in men or <39 mg/dl) (1.0 mmol/L) in women
    BMI>30 kg/m2 and/or waist:hip ratio >0.9 in men, >0.85 in women
    Urinary albumin excretion rate ≥20 µg/min or albumin: creatinine ratio ≥30 mg/g Exclusion Criteria:
  Females of childbearing potential who are pregnant, lactating or who do not employ adequate birth control procedures.
  Presence of any serious disorder including, renal, pulmonary, hepatic, gastrointestinal, endocrine/metabolic (with the exception of non-insulin dependent type 2 diabetes), hematologic/oncologic, neurologic and psychiatric diseases are exclusionary.
  History of heart failure.
  Stroke or heart attack within past 6 months.
  Use of insulin.
  Non-dominant upper arm circumference greater than 50 cm. (19.5 inches)
  Currently using any prescription or over-the-counter weight loss products
  Previous bariatric surgery or other weight reduction procedures
  Weight loss or gain of greater than 15 pounds in the last 3 months
  Past or current diagnosis of an eating disorder Demographics and Metabolic Parameters of the Study Population:

| | |
|---|---|
| Women, % | 61.5 |
| Age, y | 50.0 ± 12.5 |
| SBP, mmHg | 146.6 ± 15.3 |
| DBP, mmHg | 91.1 ± 9.7 |
| Waist circumference (cm) | 108.4 ± 15.8 |
| Total cholesterol, mg/dl | 226.6 ± 39.9 |
| LDL cholesterol, mg/dl | 154.5 ± 35.5 |
| HDL cholesterol, mg/dl | 43.0 ± 10.0 |
| Triglycerides, mg/dL | 198.3 ± 40.5 |
| Glucose, mg/dL | 105.7 ± 17.3 |

Figure 1:
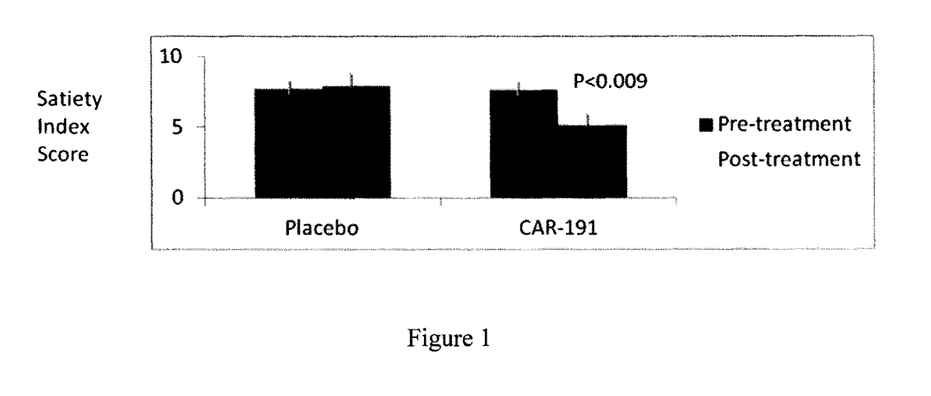
FIG. 1 illustrates results of a clinical study to test a combination of one possible embodiment of the invention, in which Berberine, LA and apocynin are shown to be an effective appetite suppressant.

Results of the Clinical Study:
Effect of CAR-191 as an Appetite Suppressant:
  Referring to FIG. 1, there is a clear reduction in satiety index score of the CAR-191 group after treatment, when compared to the group administered placebo. A detailed questionnaire was given to all participants before and after the treatment period. The questions comprised issues regarding dietary intake, feeling of satiety, changes in mood or activity, and snacking in between meals. A weighted score was given for each answer, and a satiety index score was determined. A lower score noted that improved satiety.

Serum Markers:

Blood was collected at baseline (before treatment) and 12 weeks of treatment with either placebo or CAR-191. Serum was isolated, and biomarkers were measured by using ELISA technique.

TABLE 1

Measurement of serum biomarkers

| | Placebo | | CAR-191 | |
|---|---|---|---|---|
| | Baseline | 12 weeks | Baseline | 12 weeks |
| Markers of inflammation | | | | |
| ▶ PAI-1 (ng/ml) | 257 ± 47 | 236 ± 39 | 271 ± 35 | 189 ± 29* |
| ▶ hsCRP (mg/l) | 2.1 ± 0.3 | 2.1 ± 0.4 | 2.4 ± 0.4 | 1.8 ± 0.3 |
| Markers of diabetes and insulin resistance | | | | |
| ▶ Glutathione redox ratio | 3.0 ± 0.5 | 3.2 ± 0.4 | 3.1 ± 0.5 | 2.6 ± 0.4* |
| ▶ HOMA-IR (index) | 2.3 ± 0.4 | 2.0 ± 0.4* | 2.3 ± 0.3 | 1.5 ± 0.3* |
| Direct measurement of vascular function | | | | |
| ▶ Endothelial FMD | 4.4 ± 0.7 | 4.8 ± 0.4 | 4.3 ± 0.8 | 9.5 ± 0.7* |

*value differs ($p < 0.05$) from baseline and placebo/12 weeks (time and group comparison)

Figure 2:
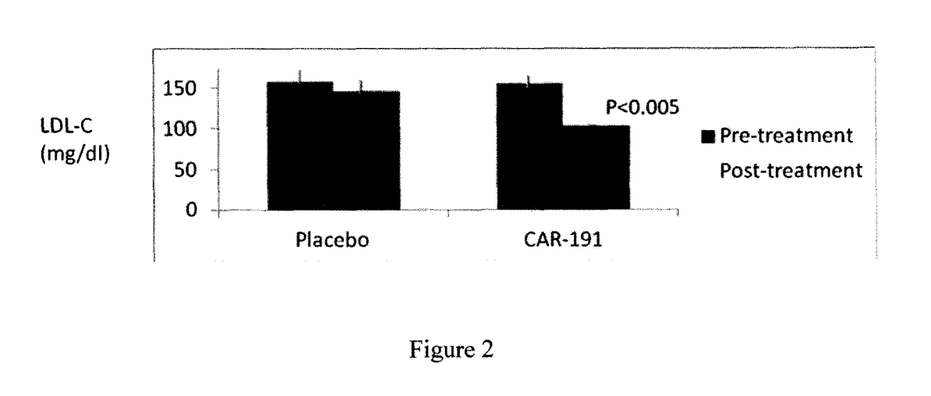
FIG. 2 illustrates results of the clinical study of FIG. 1, showing that the combination of Berberine, LA and apocynin lowers LDL cholesterol levels.

Effect of CAR-191 on LDL Cholesterol Levels:

Referring to FIG. 2, there is a clear reduction in the LDL cholesterol levels of the CAR-191 group after treatment, when compared to the group administered placebo. These results are comparable to statin therapy, in which 25-65% reduction in LDL cholesterol is noted.

Figure 3:
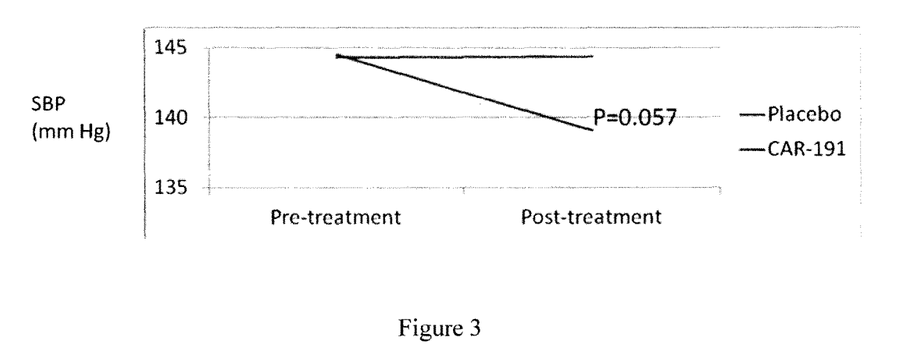
FIG. 3 illustrates results of the clinical study of FIG. 1, showing that the combination of Berberine, LA and apocynin lowers systolic blood pressure.

Effect of CAR-191 on Systolic Blood Pressure:

Referring to FIG. 3, there is a nonsignificant but a trend to reduction in the systolic blood pressure of the CAR-191 group after treatment, when compared to the group administered placebo.

Figure 4:
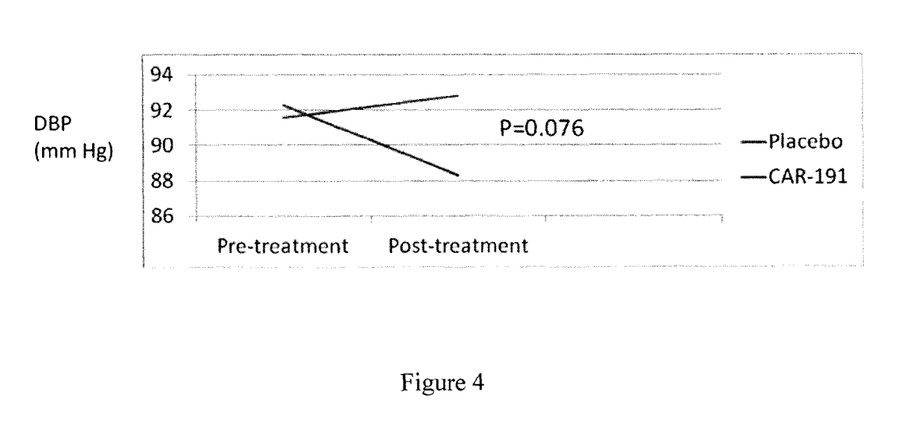
FIG. 4 illustrates results of the clinical study of FIG. 1, showing that the combination of Berberine, LA and apocynin lowers diastolic blood pressure.

Effect of CAR-191 on Diastolic Blood Pressure:

Referring to FIG. 4, there is a nonsignificant but a trend to reduction in the diastolic blood pressure of the CAR-191 group after treatment, when compared to the group administered placebo.

Effect of CAR-191 on Parameters of Body Fat:

Referring to Table 2 below, there is a measurable reduction in the both waist circumference and total body fat percentage of the CAR-191 group after treatment, observed in both males and females, as compared to the group administered placebo.

TABLE 2

Measurement of body fat parameters

| | Placebo | | CAR-191 | | |
|---|---|---|---|---|---|
| | Baseline | 12 weeks | Baseline | 12 weeks | |
| Waist Circumference (cm) | | | | | |
| ▶ Male | 117 ± 27 | 121 ± 24 | 120 ± 20 | 111 ± 21 | p = 0.082 |
| ▶ Female | 108 ± 24 | 103 ± 19 | 110 ± 17 | 105 ± 20 | p = 0.114 |
| Total body fat (percentage) | | | | | |
| ▶ Male | 39.1 ± 6.6 | 39.2 ± 7.0 | 38.1 ± 5.5 | 35.3 ± 5.5 | p = 0.077 |
| ▶ Female | 42.2 ± 7.3 | 41.8 ± 6.5 | 42.8 ± 7.0 | 40.0 ± 6.1 | p = 0.098 |

Figure 5:
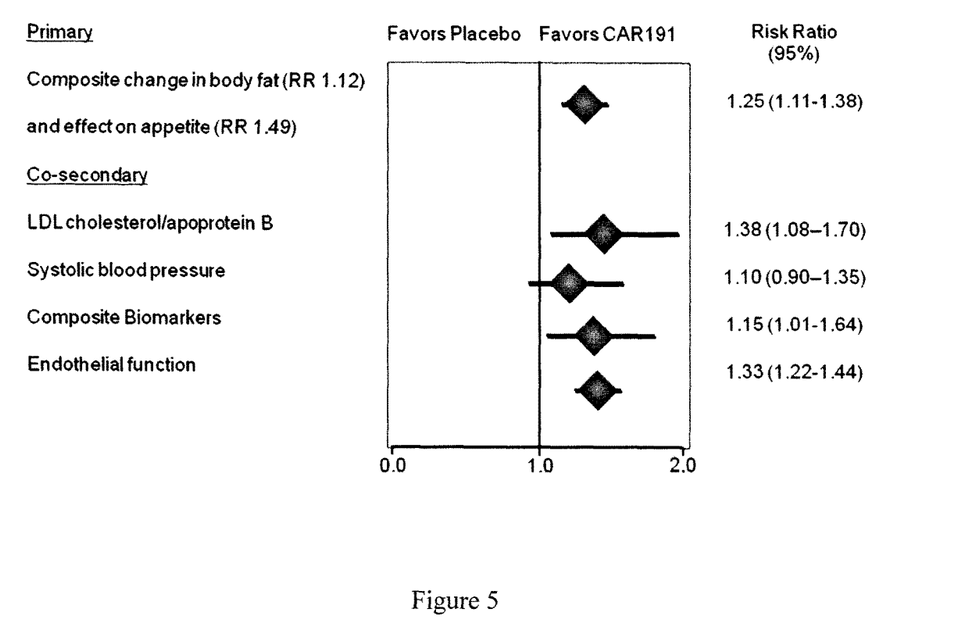
FIG. 5 illustrates results of the clinical study of FIG. 1, summarizing the primary and secondary endpoint results for the combination of Berberine, LA and apocynin.

Incidence of Primary and Secondary Endpoints:

In summary, and referring to FIG. 5, there is a clear trend in both primary and co-secondary markers tested (1: composite change in body fat, effect on appetite; 2: LDL cholesterol/apoprotein B, systolic blood pressure, composite biomarkers, endothelial function) favoring the CAR-191 group after treatment, when compared to the group administered placebo.

Tolerability of CAR-191:

Referring to Table 3 below, CAR-191 was shown to be very safe and well tolerated in the study population. Of the 42 patients who enrolled in the study, two patients experienced gastrointestinal symptoms of a mild to moderate degree, and one patient experienced a systemic rash of a moderate degree. There was no abnormality in liver function tests or renal function tests.

TABLE 3

Tolerability of CAR-191

| | |
|---|---|
| Started Study: | 42 |
| Completed Study: | 28 (66.7%) |
| Reasons Why Subjects Did Not Complete Study: | |
| Did not want to continue: | 11/14 (no adverse effects) |
| GI Symptoms: | 2/14 |
| Diffuse rash, moderate: | 1/14 |
| No adverse effects on liver function | |
| No adverse effects on renal function | |

Summary of Clinical Results and Conclusions:

Treatment with CAR-191 was well tolerated throughout the study, and met the primary endpoint (suppression of appetite and parameters of weight and diet) and several secondary endpoints. A rigorous protocol was followed utilizing maximal dosage of pharmaceutical as indicated. It is important to bear in mind that this is a high risk population of patients, and the efficacy of CAR-191 treatment was significant.

Thus, the findings indicate that CAR-191 is a safe and effective agent in impacting individuals who are at risk at least for diabetes mellitus, hypertension and dyslipidemia, all of which are serious indicators of cardio and renovascular diseases. In addition, CAR-191 can be used as adjunctive management or primary management for individuals who are unable or unwilling to take pharmaceutical drugs.

One or more currently preferred embodiments have been described by way of example. It will be apparent to persons skilled in the art that a number of variations and modifications can be made without departing from the scope of the invention as defined in the claims.

What is claimed is:

1. A method of treating a cardiometabolic disease or disorder, said method comprising administering:
   100 mg to 400 mg Berberine,
   75 mg to 300 mg alpha lipoic acid (LA),
   and 50 mg to 200 mg *Picrorhiza*,
   to a human subject in need thereof in an amount sufficient to ameliorate said cardiometabolic disease or disorder in said subject.

2. The method of claim 1, wherein said Berberine, LA, and *Picrorhiza* are administered in amounts of about 200 mg Berberine, about 150 mg LA, and about 100 mg *Picrorhiza* per dose.

3. The method of claim 1, wherein said Berberine, LA, and *Picrorhiza* are administered 3 times a day, before breakfast, lunch and dinner.

4. The method of claim 1, wherein said cardiometabolic disease or disorder is dyslipidemia.

5. A method of reducing LDL levels in a human subject in need thereof, said method comprising administering 100 mg to 400 mg Berberine, from 75 mg to 300 mg LA and from 50 mg to 200 mg *Picrorhiza* per dose, up to 3 times daily, wherein said LDL levels are reduced.

6. The method of claim 5, wherein said Berberine, LA, and *Picrorhiza* are administered in amounts of about 200 mg Berberine, about 150 mg LA, and about 100 mg *Picrorhiza* per dose.

7. The method of claim 5, wherein said Berberine, LA, and *Picrorhiza* are administered 3 times a day, before breakfast, lunch and dinner.

* * * * *